(12) United States Patent
Radzinsky

(10) Patent No.: US 11,266,515 B2
(45) Date of Patent: Mar. 8, 2022

(54) ADAPTOR FOR LAMINATED STUMP SOCKET OF PROSTHETIC LIMB

(71) Applicant: Vladimir Radzinsky, Torrance, CA (US)

(72) Inventor: Vladimir Radzinsky, Torrance, CA (US)

( * ) Notice: Subject to any disclaimer, the term of this patent is extended or adjusted under 35 U.S.C. 154(b) by 0 days.

(21) Appl. No.: 17/024,475

(22) Filed: Sep. 17, 2020

(65) Prior Publication Data

US 2021/0077282 A1 Mar. 18, 2021

Related U.S. Application Data

(60) Provisional application No. 62/901,639, filed on Sep. 17, 2019.

(51) Int. Cl.
| | | |
|---|---|---|
| *A61F 2/80* | (2006.01) | |
| *A61F 2/76* | (2006.01) | |
| *A61F 2/50* | (2006.01) | |
| *A61F 2/78* | (2006.01) | |

(52) U.S. Cl.
CPC .............. *A61F 2/80* (2013.01); *A61F 2/5044* (2013.01); *A61F 2/76* (2013.01); *A61F 2002/7881* (2013.01)

(58) Field of Classification Search
CPC .. A61F 2/5044; A61F 2/76; A61F 2/80; A61F 2002/5052; A61F 2002/5053; A61F 2002/5055; A61F 2002/5056; A61F 2/60; A61F 2/54
See application file for complete search history.

(56) References Cited

U.S. PATENT DOCUMENTS

| | | |
|---|---|---|
| 5,201,773 A | 4/1993 | Carideo, Jr. |
| 5,545,232 A | 8/1996 | Van de Veen |
| 5,593,456 A | 1/1997 | Merlette |
| 6,340,370 B1 | 1/2002 | Willert et al. |
| 7,722,679 B2 | 5/2010 | Radzinsky |
| 2003/0171818 A1 | 9/2003 | Lewallen |
| 2004/0102856 A1 | 5/2004 | Hellberg |
| 2004/0204770 A1* | 10/2004 | Curtis .................. A61F 2/5046 623/33 |
| 2010/0228361 A1* | 9/2010 | Radzinsky ............... A61F 2/80 623/33 |

FOREIGN PATENT DOCUMENTS

DE 102016108043 A1 * 11/2017 ............... A61F 2/80

OTHER PUBLICATIONS

Translation of DE102016108043-A. Johan Nieuwendijk. (Year: 2017).*

* cited by examiner

*Primary Examiner* — Christie L Bahena

(57) ABSTRACT

A method of forming a stump socket is disclosed. The method includes obtaining a stump casting, obtaining a socket adaptor, positioning the socket adaptor on a distal end of the stump casting, and applying a binder material to encapsulate the socket adaptor. A socket adaptor may have a main body and multiple flanges. Each of the flanges may have a proximal end and a distal end. The proximal end may pivotably connect to the main body. Accordingly, pivoting of the flanges with respect to the main body may enable the socket adaptor to better and more easily conform to the stump casting.

13 Claims, 24 Drawing Sheets

ADAPTOR FOR LAMINATED STUMP SOCKET OF PROSTHETIC LIMB

RELATED APPLICATIONS

This application claims the benefit of U.S. Provisional Patent Application Ser. No. 62/901,639 filed Sep. 17, 2019, which is hereby incorporated by reference.

BACKGROUND

Field of the Invention

This invention relates to socket adaptors for attaching prosthetic limbs and, more particularly, to novel systems and methods for socket adaptors that conform to stump castings.

Background Art

Adaptors are used in the prosthetic industry in the creation of stump sockets. When fit over the stump of a patient, a stump socket provides an attachment location for a prosthetic device. Accordingly a stump socket must fit comfortably on the stump of the patient and have sufficient structural integrity to create a reliable connection to the prosthetic device. Given the current state of the art, what is needed are adaptors that are more easily incorporated within a stump socket.

BRIEF DESCRIPTION OF THE DRAWINGS

The features of the present invention will become apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

Figure 1:
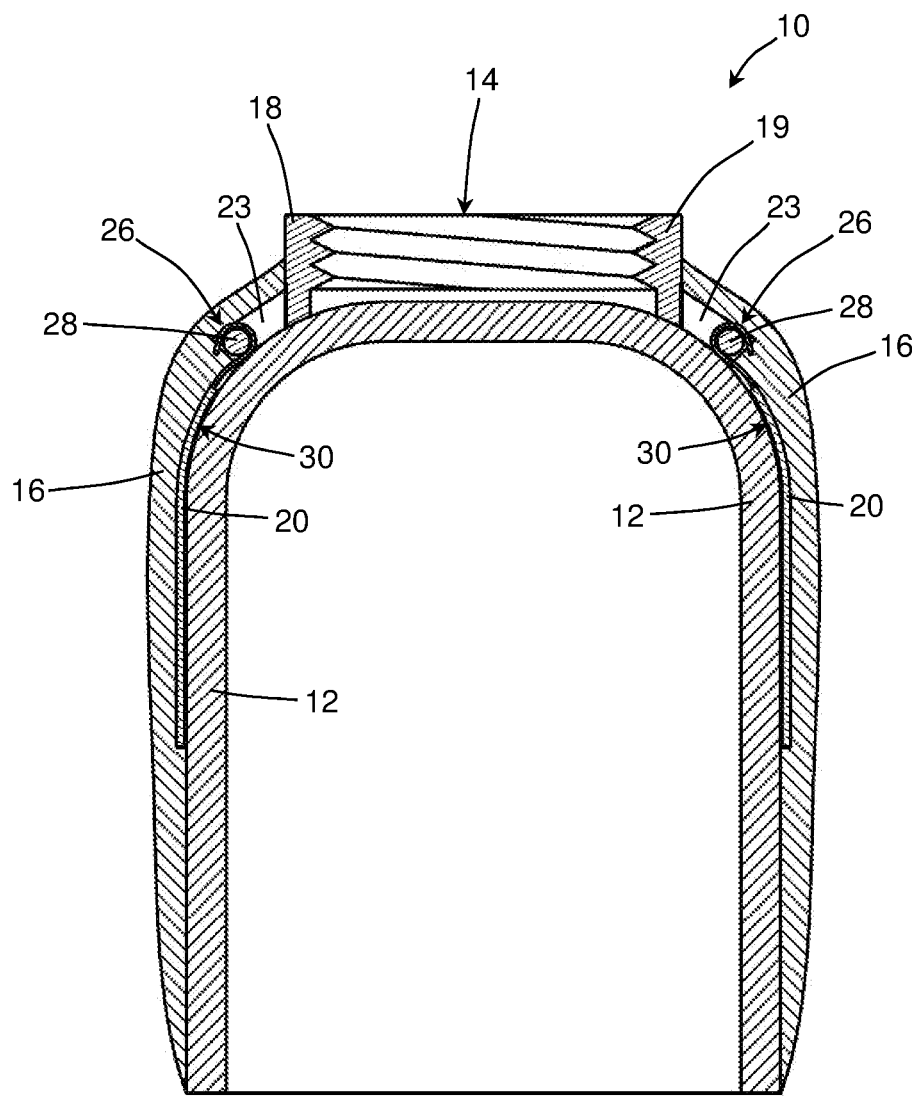
FIG. 1 is a side cross-sectional view of one embodiment of a stump socket in accordance with the present invention applied to (or being formed on) a stump casting.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

U.S. Pat. No. 7,722,679 issued May 25, 2010 and U.S. Patent Application Publication No. 2010/0228361 published Sep. 9, 2010 are each hereby incorporated by reference.

Figure 2:
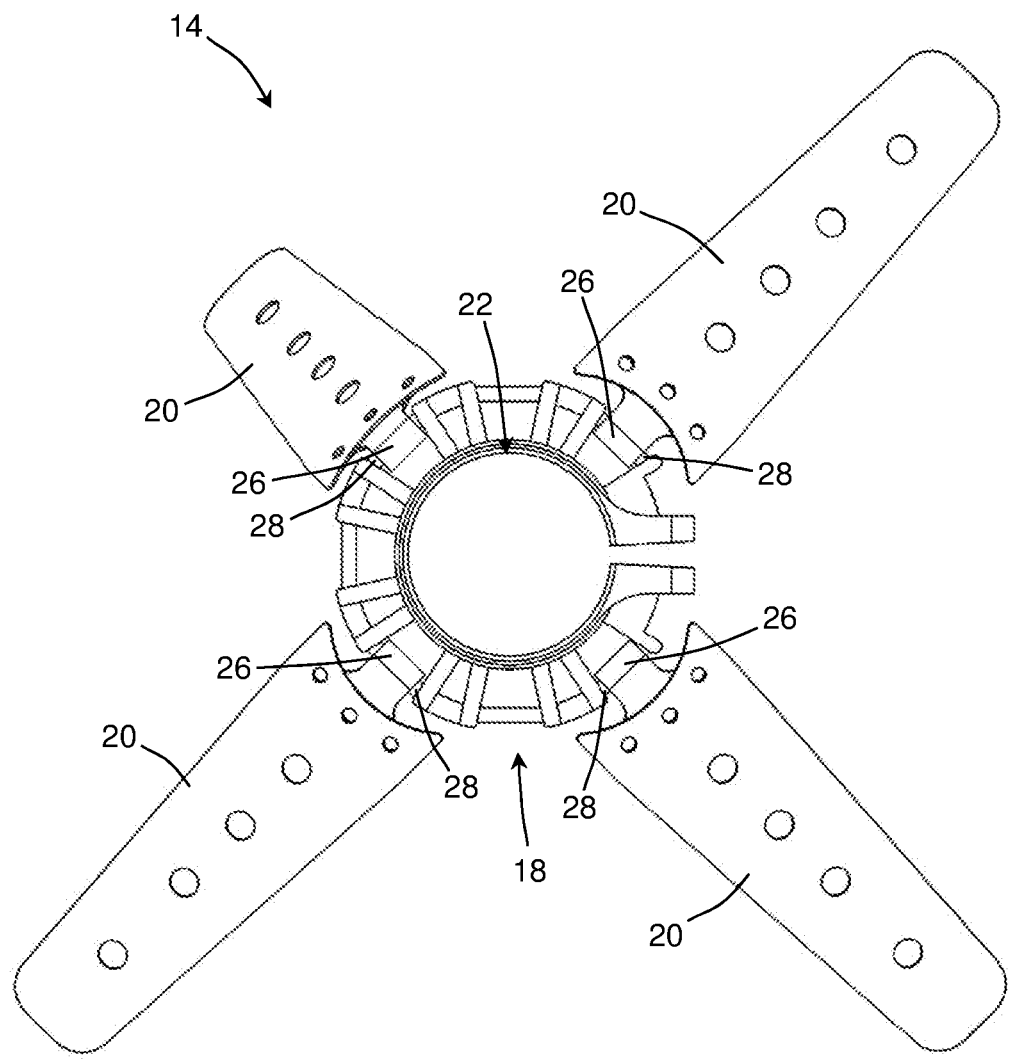
FIG. 2 is a top perspective view of one embodiment of a socket adaptor in accordance with the present invention.
Figure 3:
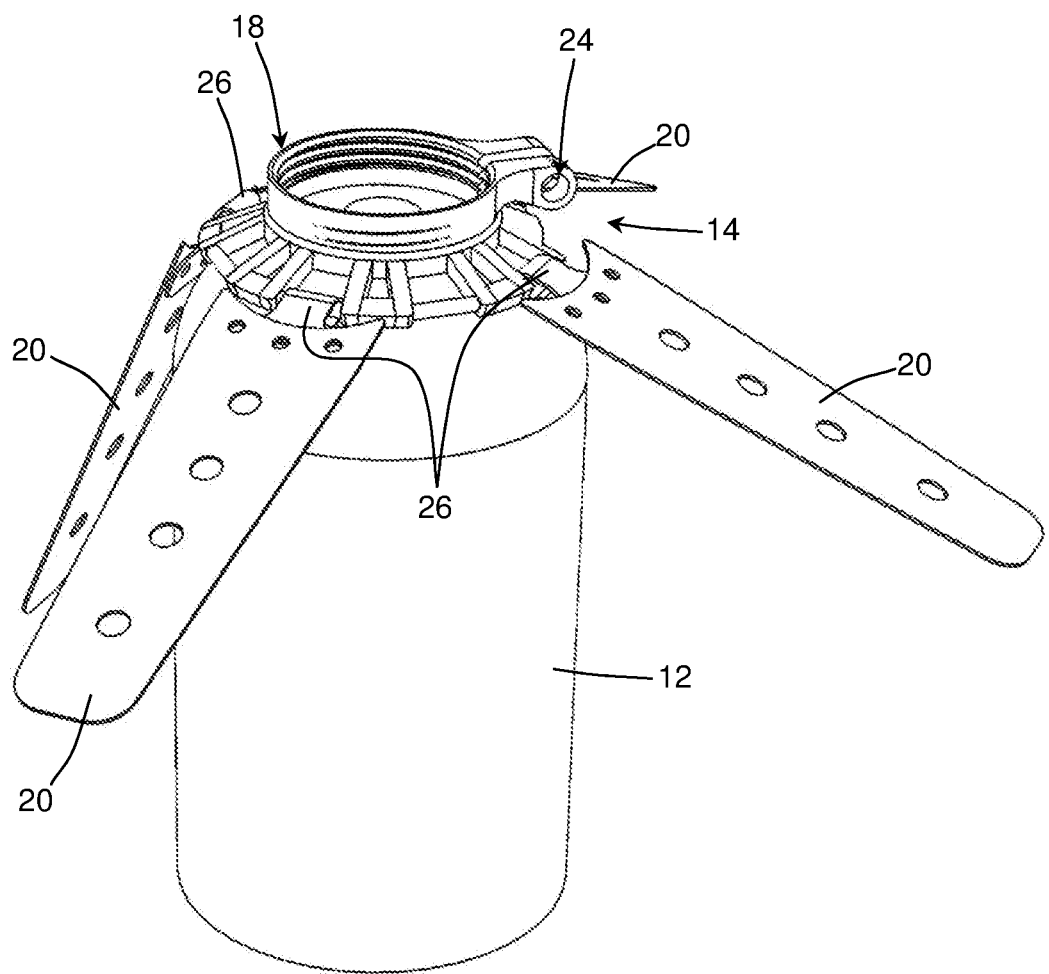
FIG. 3 is a perspective view of the socket adaptor of FIG. 2 being applied to a stump casting in accordance with the present invention.
Figure 4:
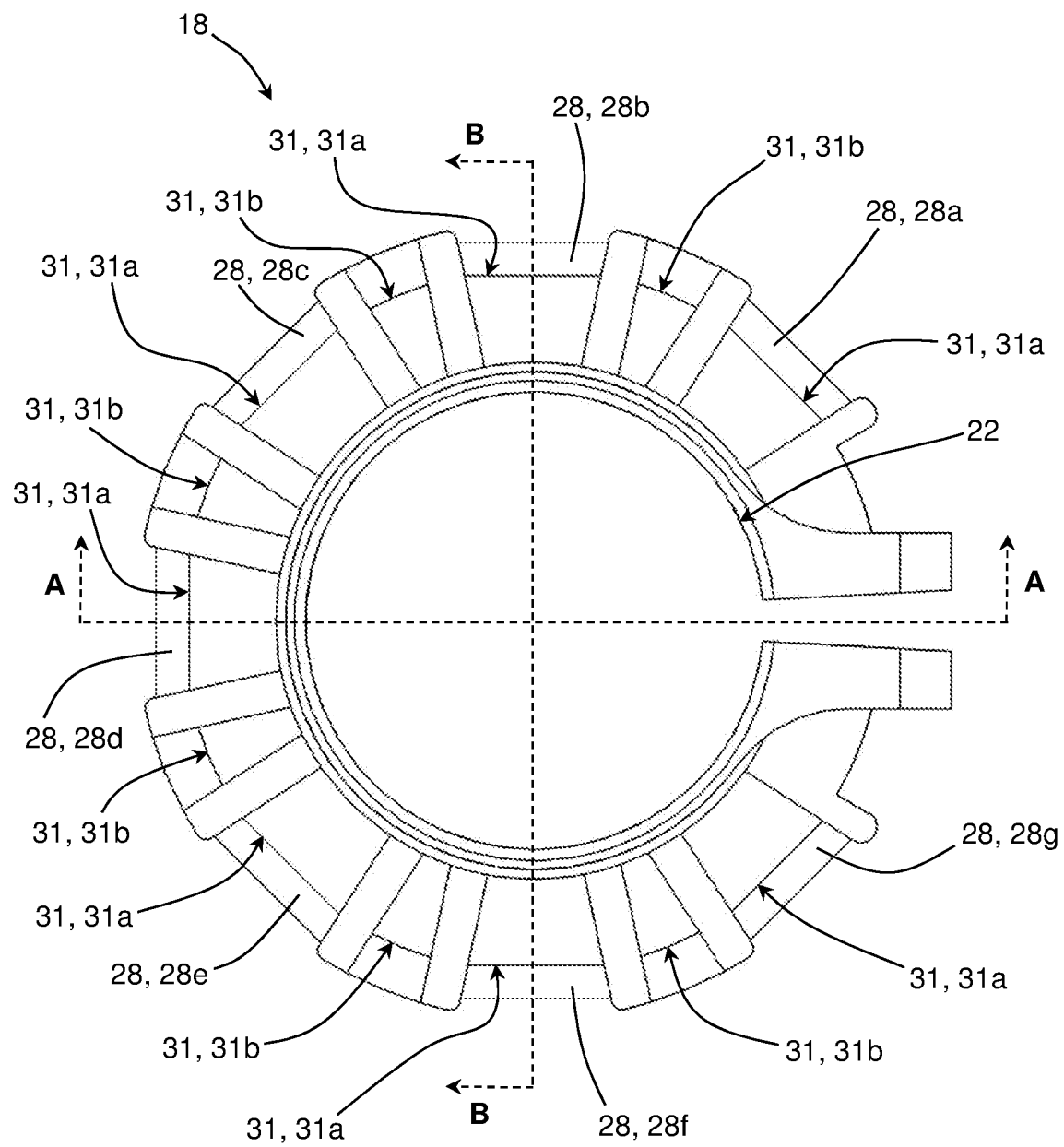
FIG. 4 is a top view of the main body of the socket adaptor of FIG. 2.
Figure 5:
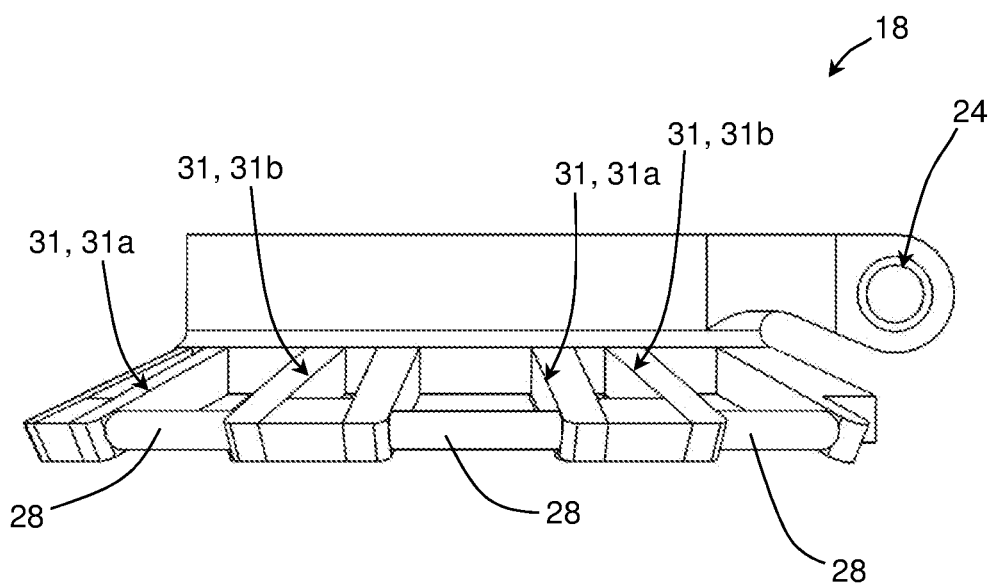
FIG. 5 is a first side view of the main body of the socket adaptor of FIG. 2.
Figure 6:
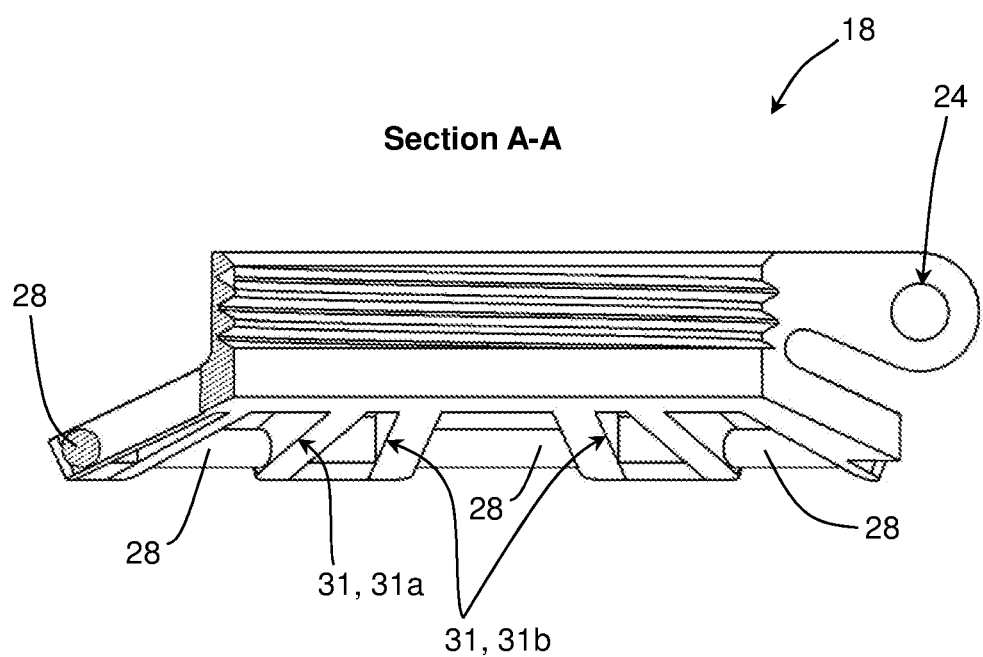
FIG. 6 is a cross-sectional view of the main body of the socket adaptor of FIG. 2.
Figure 7:
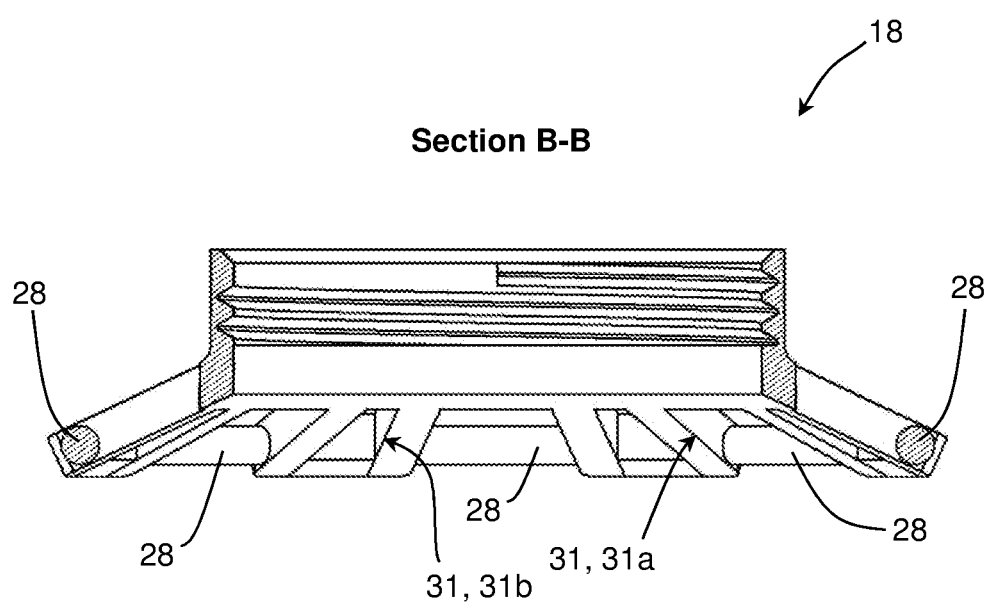
FIG. 7 is another cross-sectional view of the main body of the socket adaptor of FIG. 2.
Figure 8:
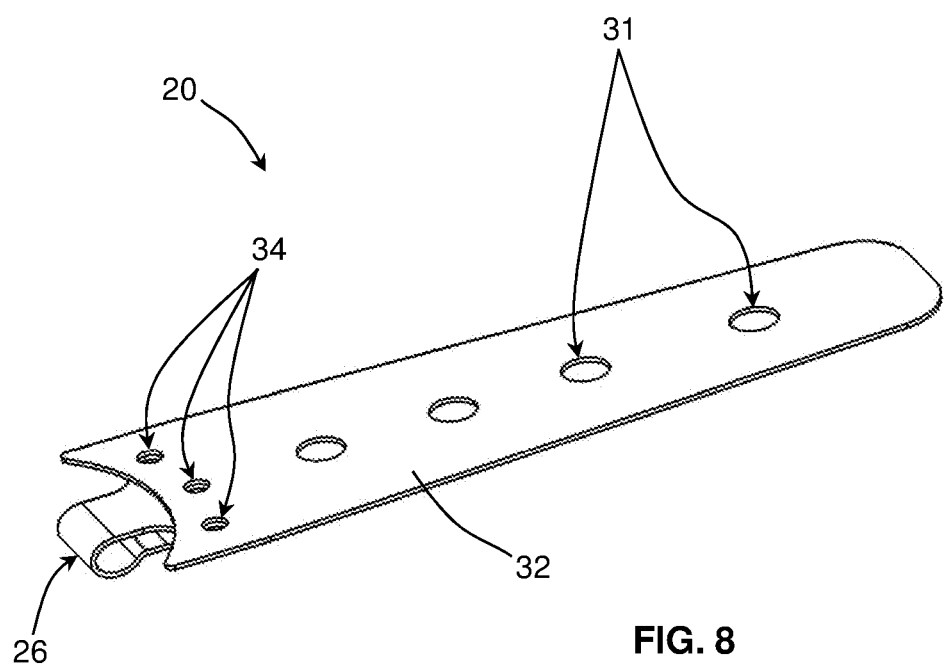
FIG. 8 is a perspective view of a flange of the socket adaptor of FIG. 2.
Figure 9:
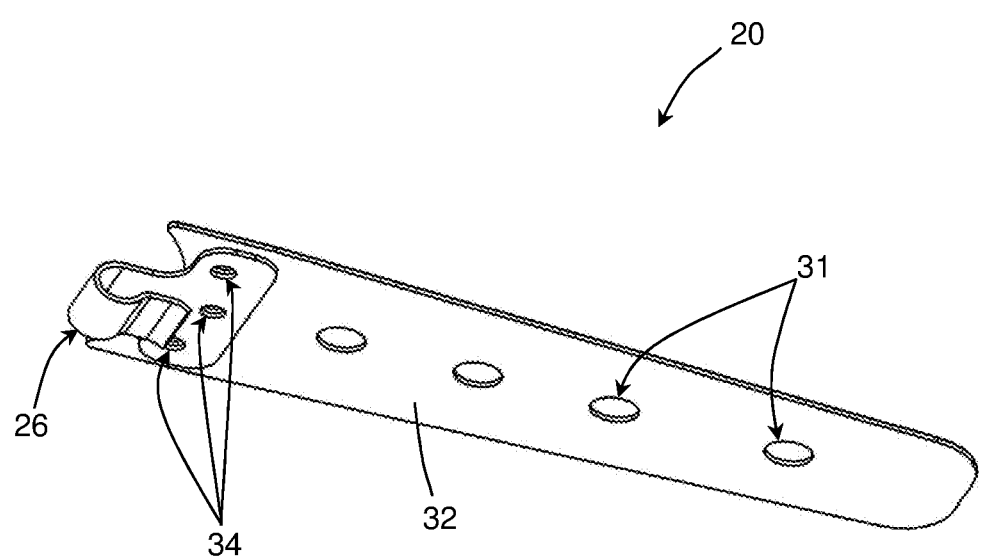
FIG. 9 is another perspective view of a flange of the socket adaptor of FIG. 2.
Figure 10:
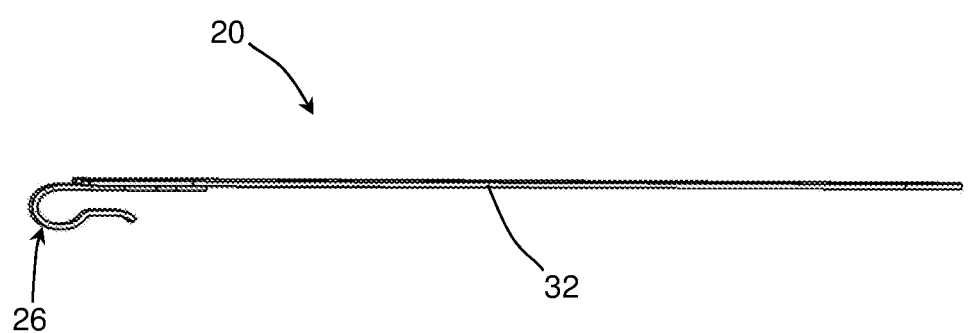
FIG. 10 is a side view of a flange of the socket adaptor of FIG. 2.
Figure 11:
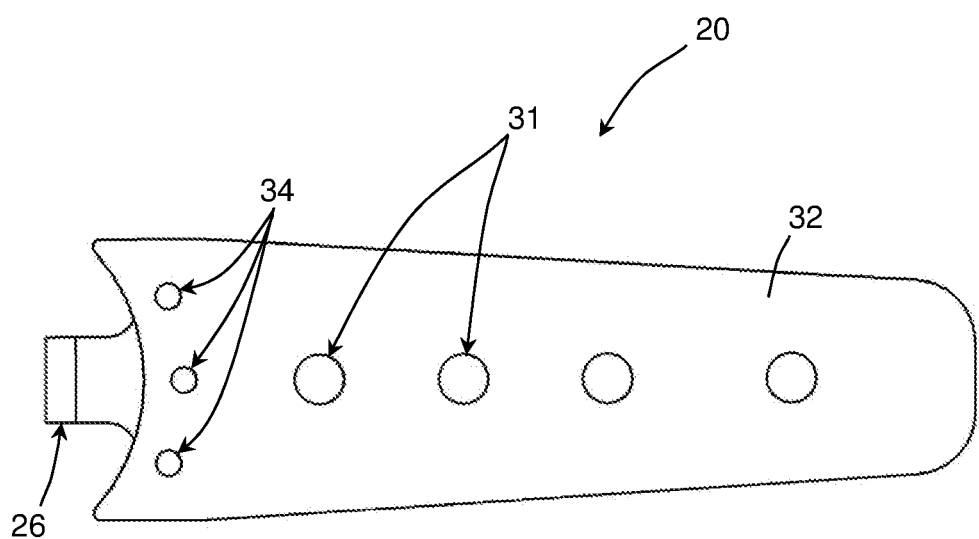
FIG. 11 is a top view of a flange of the socket adaptor of FIG. 2.
Figure 12:
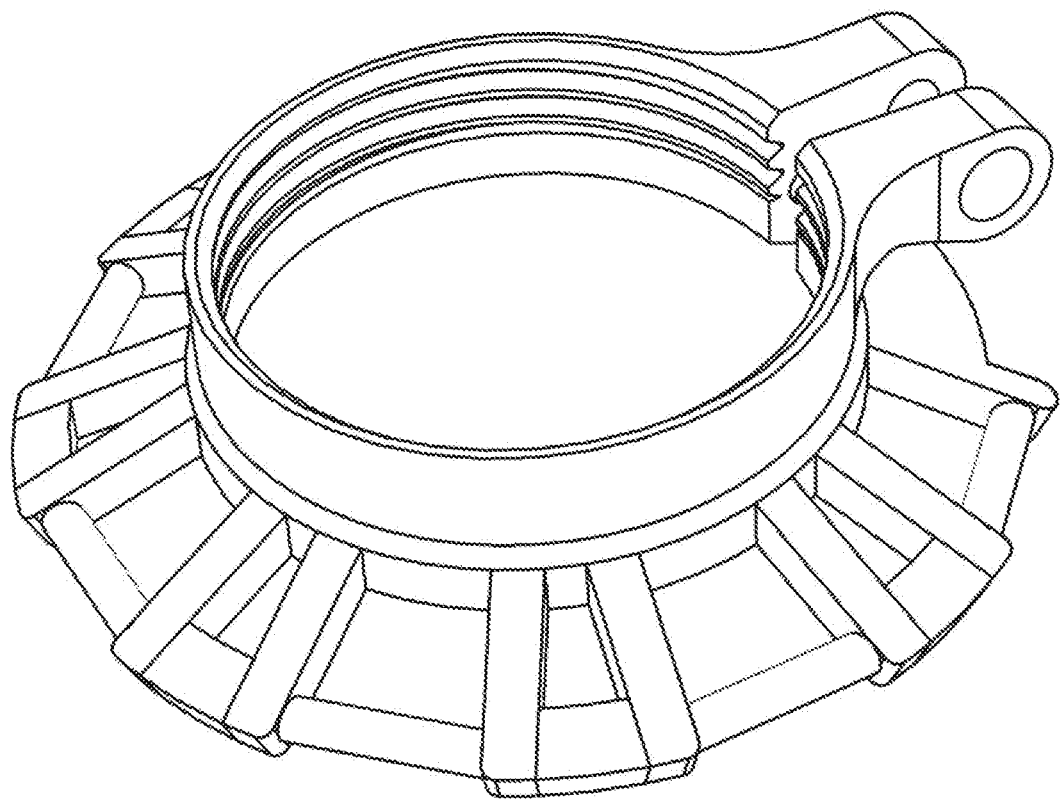
FIG. 12 is a top perspective view of the main body of the socket adaptor of FIG. 2.
Figure 13:
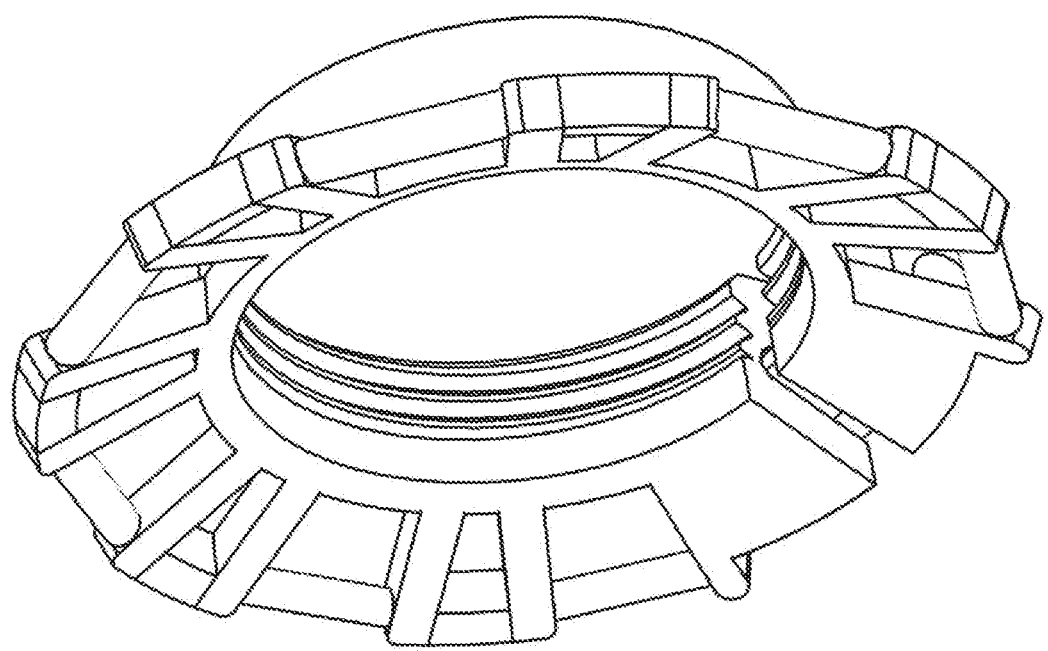
FIG. 13 is a bottom perspective view of the main body of the socket adaptor of FIG. 2.
Figure 14:
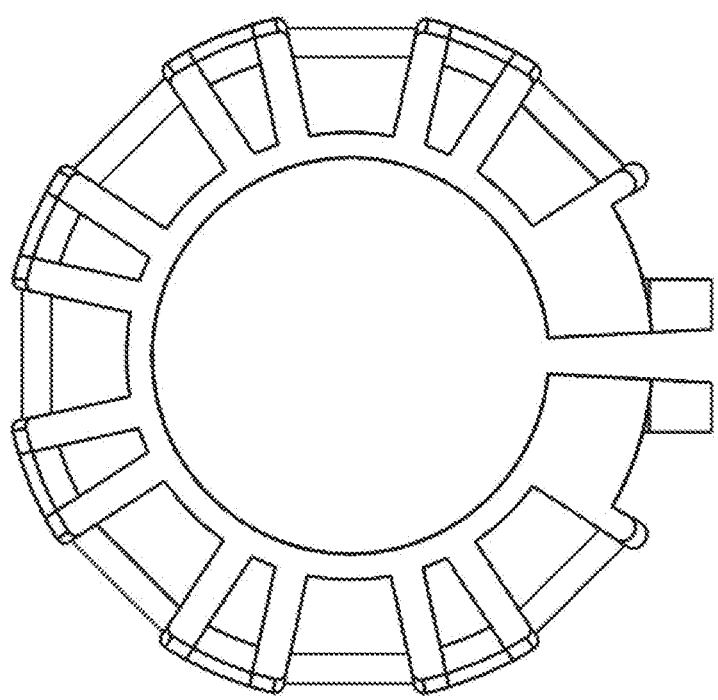
FIG. 14 is a bottom view of the main body of the socket adaptor of FIG. 2.
Figure 15:
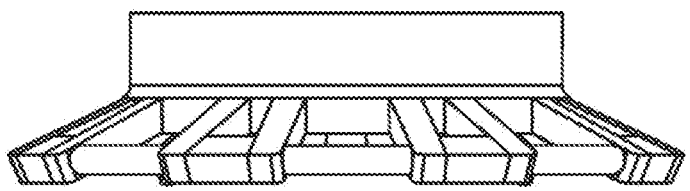
FIG. 15 is a front view of the main body of the socket adaptor of FIG. 2.
Figure 16:
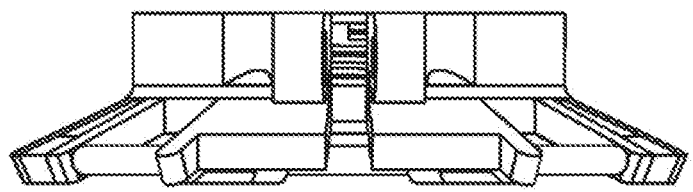
FIG. 16 is a back view of the main body of the socket adaptor of FIG. 2.
Figure 17:
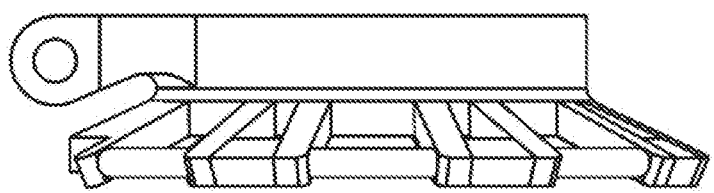
FIG. 17 is a second, opposite side view of the main body of the socket adaptor of FIG. 2.
Figure 18:
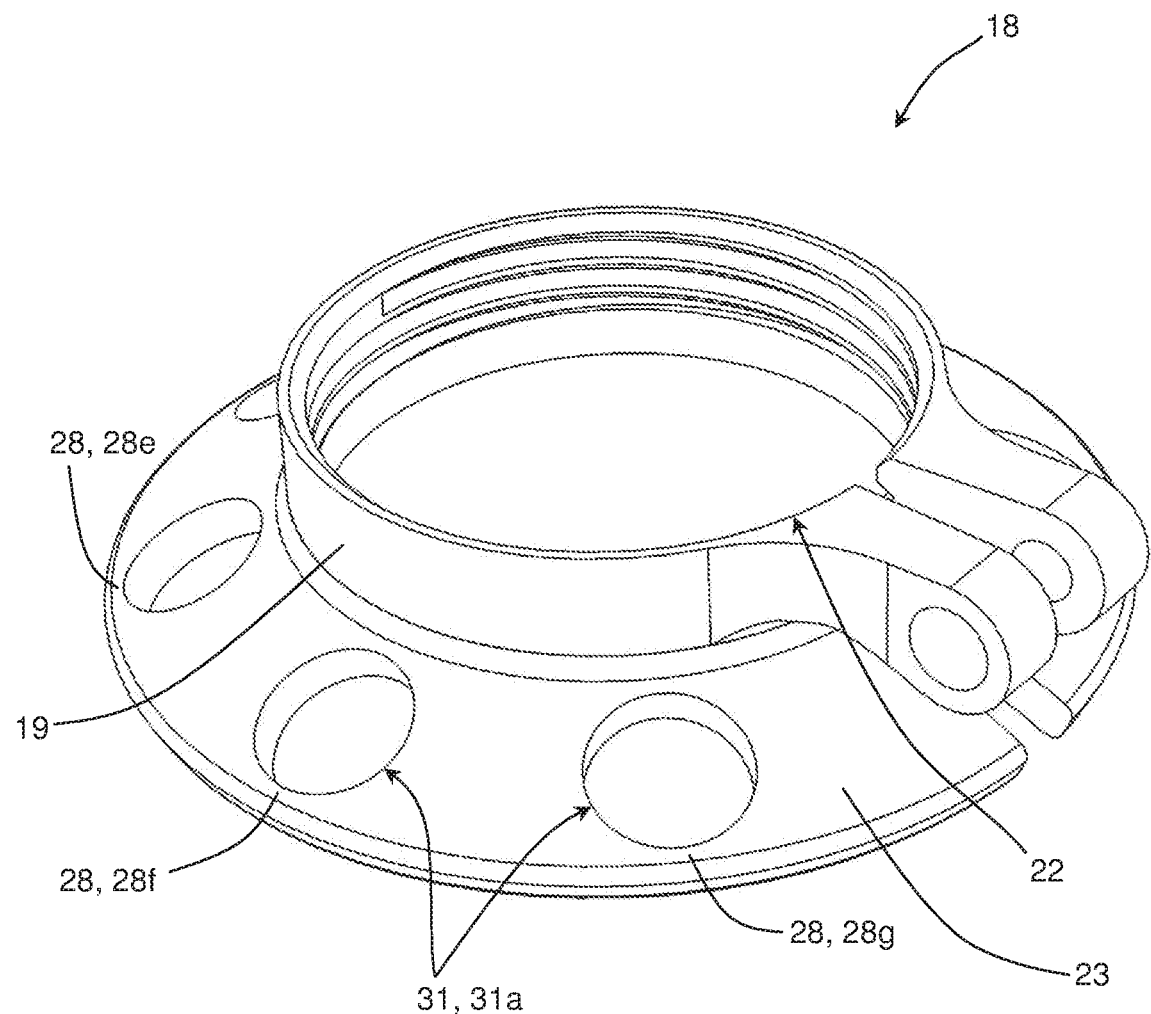
FIG. 18 is a top perspective view of an alternative embodiment of a main body of a socket adaptor in accordance with the present invention.
Figure 19:
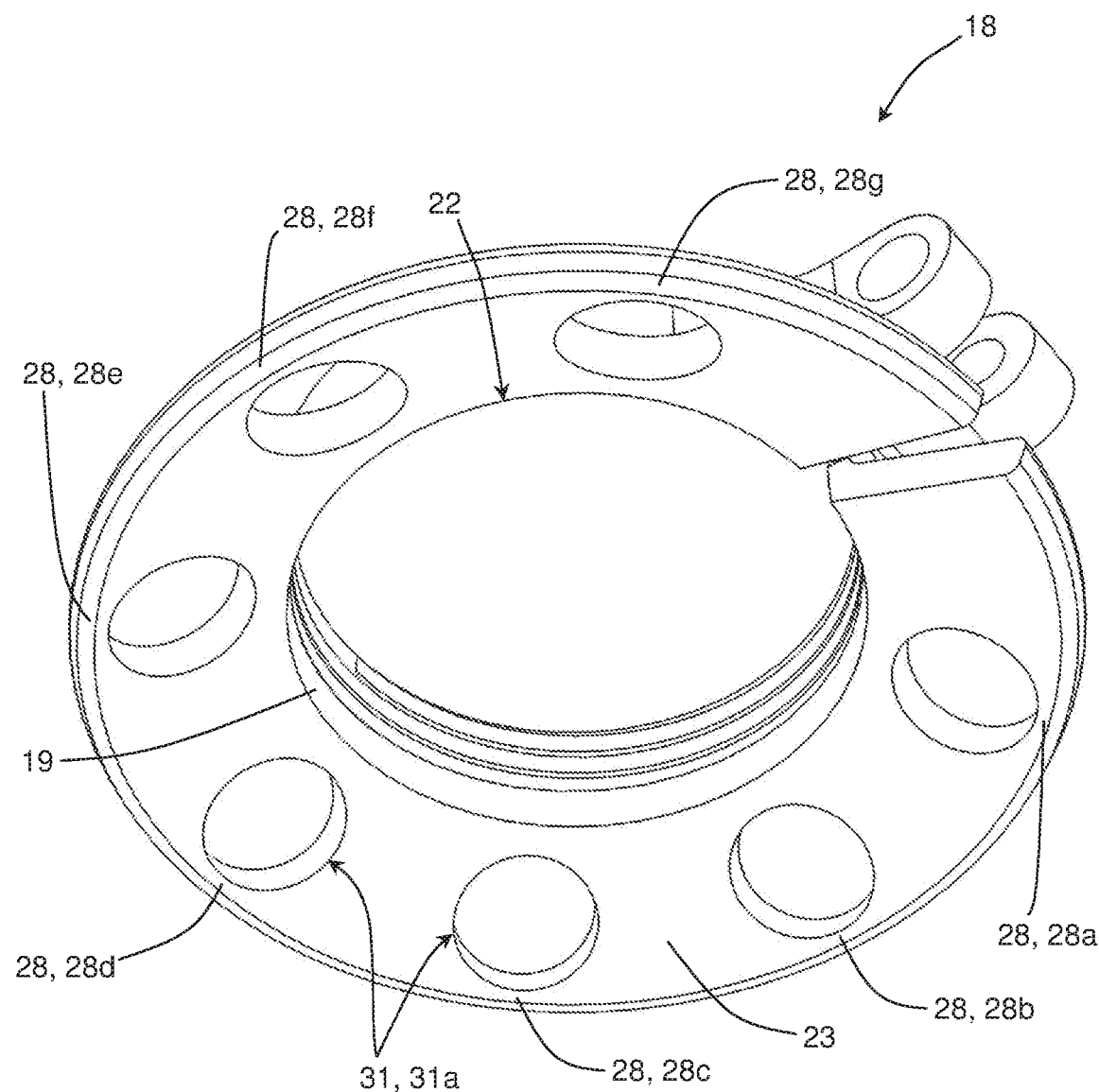
FIG. 19 is a bottom perspective view of the main body of FIG. 18.
Figure 20:
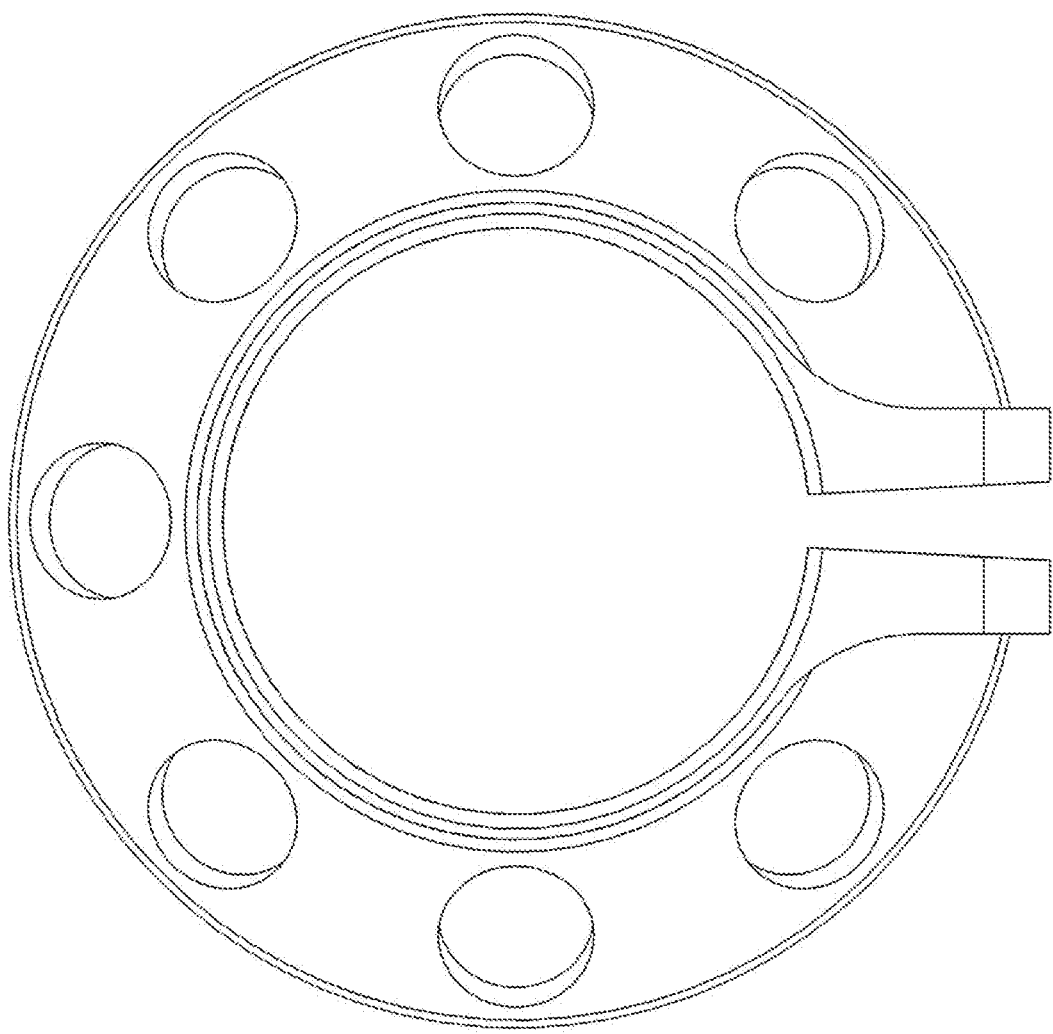
FIG. 20 is a top view of the main body of FIG. 18.
Figure 21:
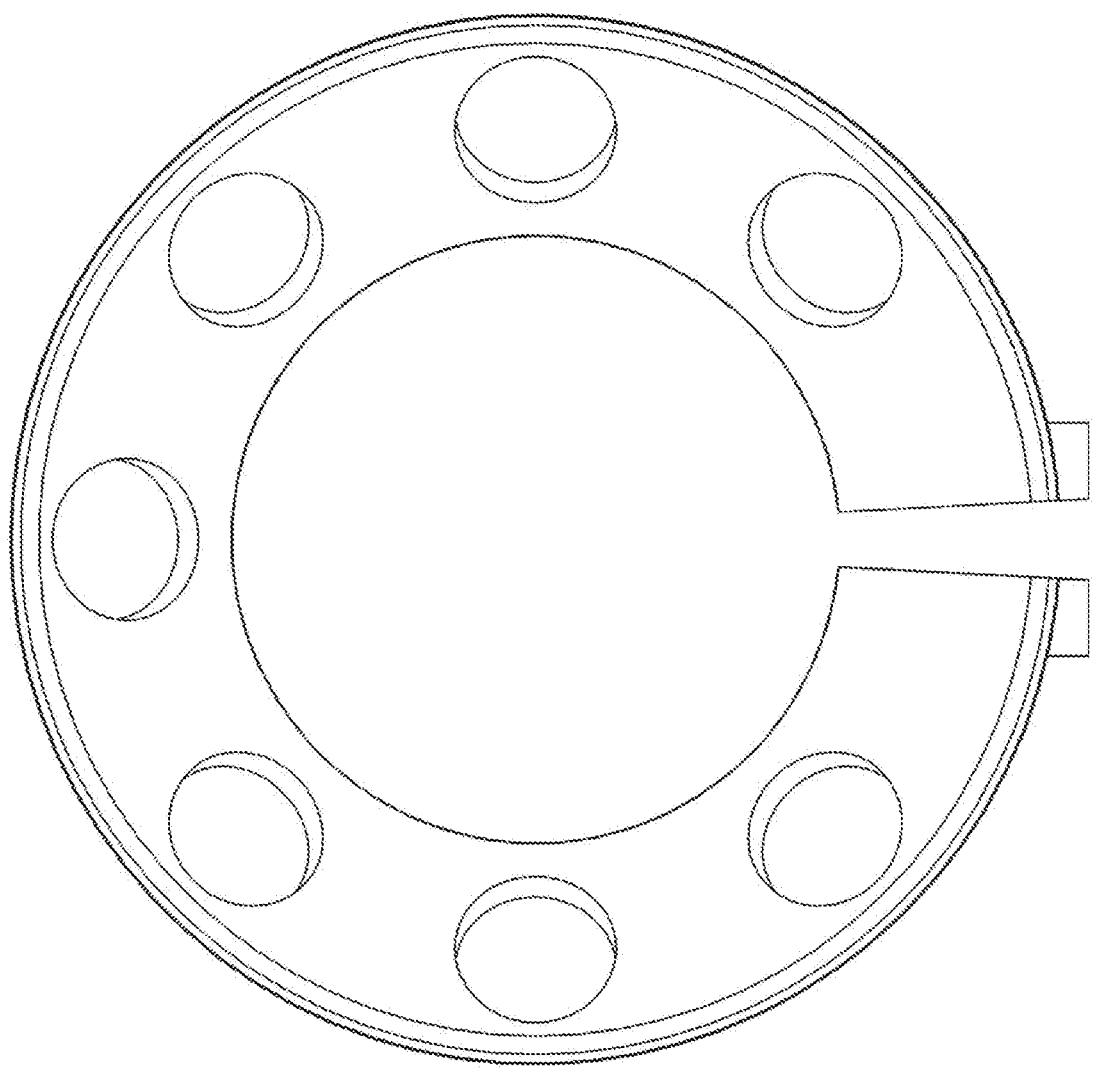
FIG. 21 is a bottom view of the main body of FIG. 18.
Figure 22:
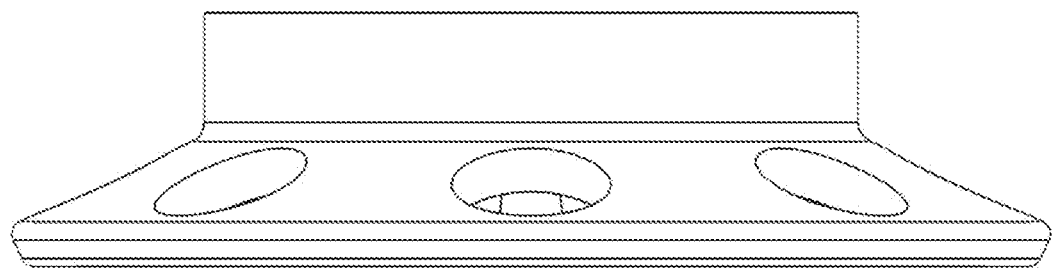
FIG. 22 is a front view of the main body of FIG. 18.
Figure 23:
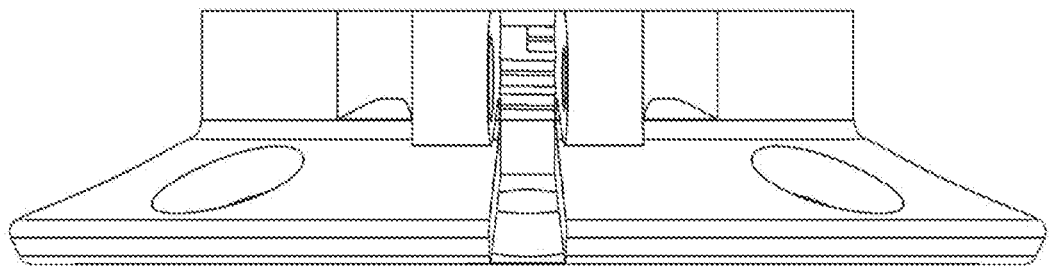
FIG. 23 is a back view of the main body of FIG. 18.
Figure 24:
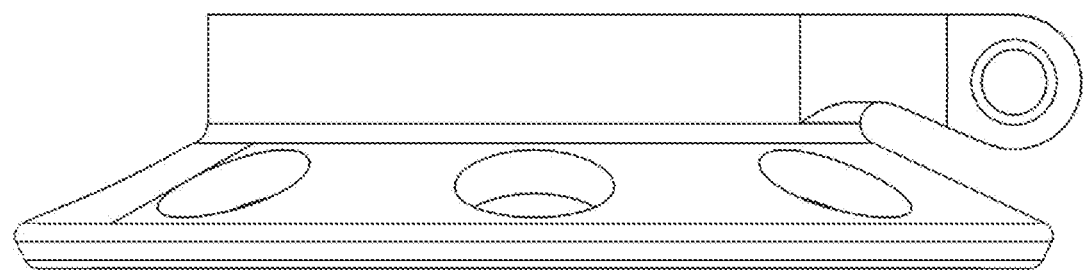
FIG. 24 is a first side view of the main body of FIG. 18.
Figure 25:
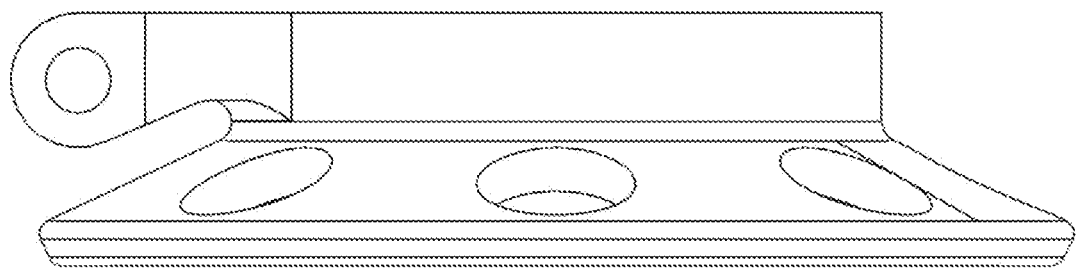
FIG. 25 is a second, opposite side view of the main body of FIG. 18.
Figure 26:
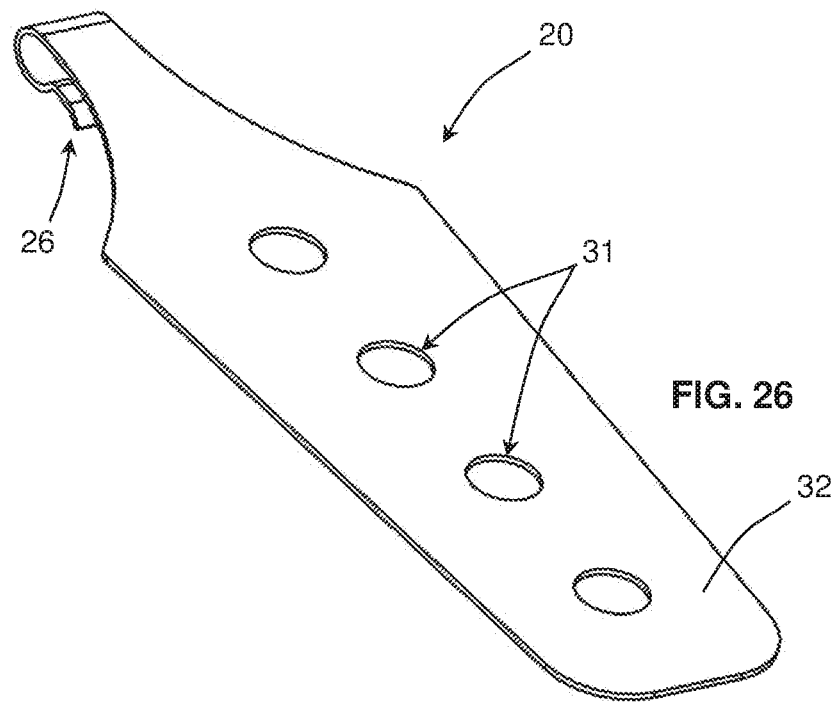
FIG. 26 is a top perspective view of an alternative embodiment of a flange of a socket adaptor in accordance with the present invention.
Figure 27:
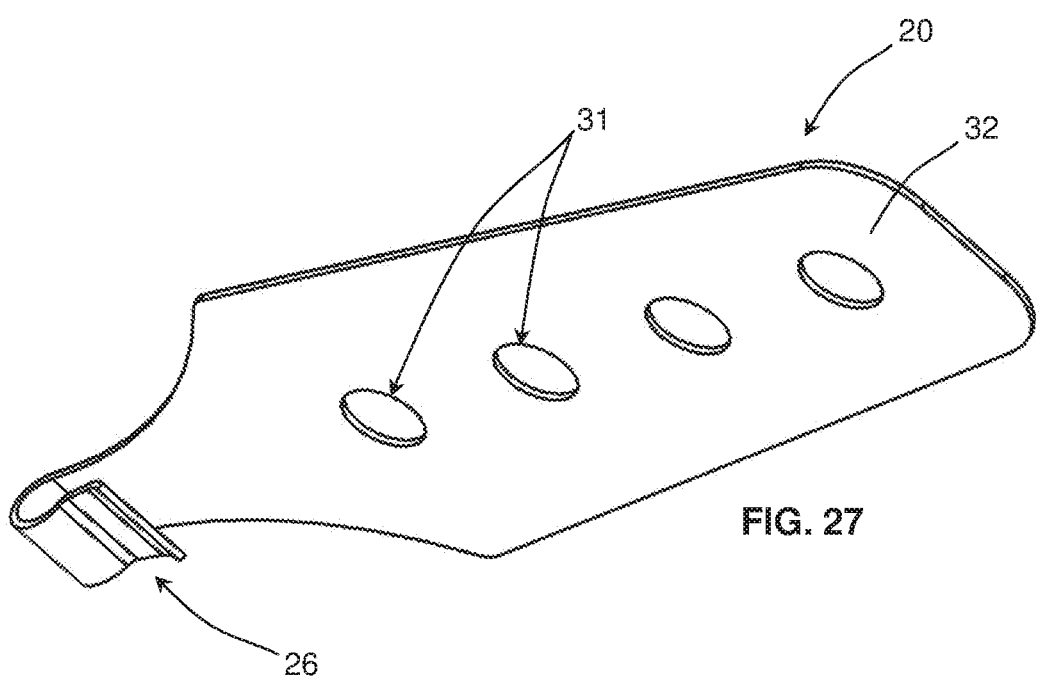
FIG. 27 is a bottom perspective view of the flange of FIG. 26.
Figure 28:
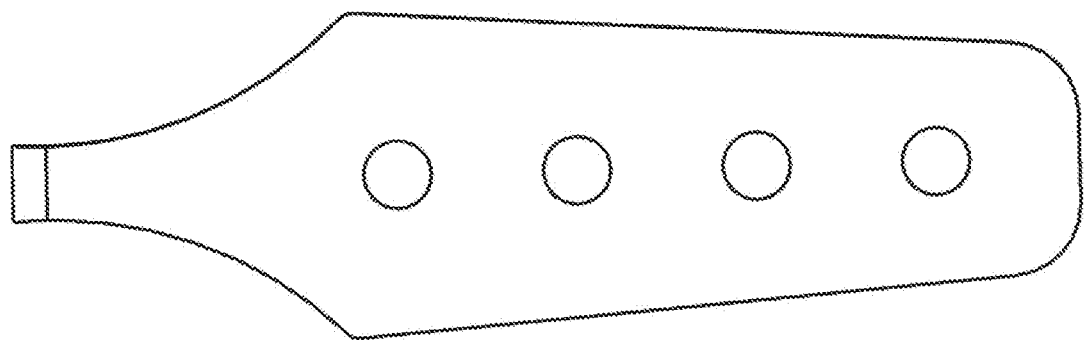
FIG. 28 is a top view of the flange of FIG. 26.
Figure 29:
FIG. 29 is a side view of the flange of FIG. 26.
Figure 30:
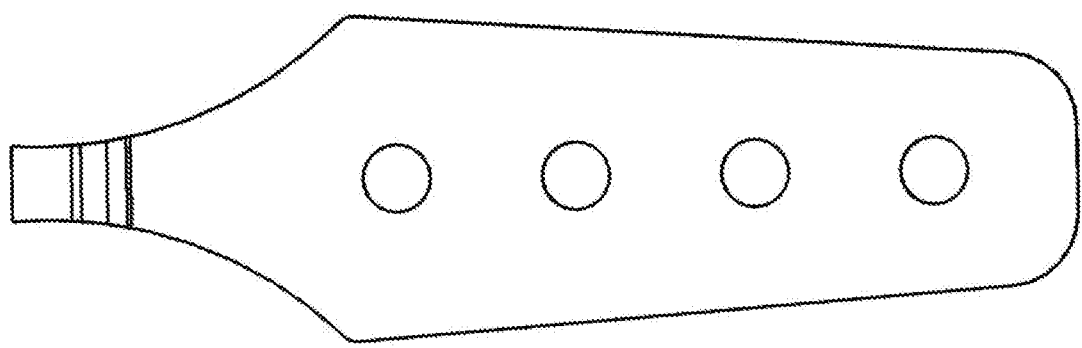
FIG. 30 is a bottom view of the flange of FIG. 26.

Referring to FIGS. 1-3, in selected embodiments, a laminated stump socket 10 in accordance with the present invention may be built over a stump casting 12 and include a socket adaptor 14 and binding material 16 (e.g., a composite overwrap material) engaging the socket adaptor 12 and forming the stump socket 10. A stump casting 12 may be created from a stump of a patient for which the laminated stump socket 10 is intended. The creation of the stump casting 12 allows a prosthetist to work without requiring the patient to be present and thereby facilitates making a laminated stump socket 10 that precisely fits the stump of the patient.

In selected embodiments, a binding material may comprise a graphite mesh 50 that is coated or impregnated with resin to encapsulate the socket adaptor 10 and create a hardened, shell-like surface, which is then removed from the stump casting 12. The end result may be a laminated stump socket 10 that is permanently formed to fit the stump of the patient.

In certain embodiments, a socket adaptor 12 may include a main body 18 and one or more flanges 20 extending outward from the main body 18. A main body 18 may include a core 19 having a main bore 22 or central aperture 22 extending therethrough. A main bore 22 may be internally threaded and selectively adjustable in diameter. For example, an adjustment screw (not shown) may engage an aperture 24 in a main body 18 in order to reduce a diameter of a main bore 22. Accordingly, after a device (e.g., a "pyramid" plug or other component for securing a prosthetic element) is threaded into a main bore 22, an adjustment screw may be turned within an aperture 24 in a main body 18 in order to reduce a diameter of the main bore 22 and secure (e.g., lock) the device therewithin.

A main body 18 may further include skirting 23. Skirting 23 may connect to a core 19 (e.g., be a monolithic extension of a core 19). For example, skirting 23 may be formed together with a core 19 in a machining, casting, or additive manufacturing process. Skirting 23 may extending away from a core 19. In certain embodiments, skirting 23 may at least partially encircle a core 19.

One or more flanges 20 may extend outwardly from a main body 18. A flange 20 may pivotably engage a main body 18 (e.g., pivotably engage an outer edge of a skirting 23 of a main body 18). Accordingly, in an uninstalled configuration, one or more flanges 20 may be free to extend axially, radially, or some combination of axially and radially away from a main body 18. In selected embodiments, a pivotable engagement between a flange 20 and a main body 18 may include a loop 26, hook 26, or the like corresponding to or extending from the flange 20 and a bar 28, dowel 28, or the like forming part of main body 18. The loop 26, hook 26, or the like may at least partially encircle the bar 28, dowel 28, or the like to enable pivoting of the corresponding flange 20 with respect to the main body 18.

A flange 20 may be broad and flat and have a curved extremity (e.g., rounded distal corners). A socket adaptor 14 may be manufactured such that one or more flanges 20 initially may be free to pivot with respect to a main body 18. Accordingly, as a socket adaptor 14 is applied to a stump casting 12 (e.g., a distal end of a stump casting 12), pivoting of one or more flanges 20 may enable those flanges 20 to drape over and somewhat follow (e.g., begin to follow) the contours of the stump casting 12. Additionally, one or more flanges 20 may be flexible and bendable. Accordingly, whatever tracking or following of the flanges 20 along a stump casting 12 cannot be accommodated with pivoting of the flanges 20 (i.e., pivoting of the flanges 20 with respect to the main body 18) may be accommodated with bending 30 of the flanges 20. Thus, while bending 30 of the one or more flanges 20 may enable them to be set as desired by a prosthetist in fitting the patient, pivoting of the flanges 20 with respect to the main body 18 may greatly reduce the amount of bending 30 that the prosthetist need impose on the flanges 20

In certain embodiments, to facilitate such bending 30, one or more flanges 20 may be made of sheet metal (e.g., sheet titanium, sheet stainless steel, or the like). Sheet metal may make the flanges 20 extremely strong and yet susceptible to bending (e.g., susceptible to controlled bending without cracking or weakening of the metal). A suitable thickness for the sheet metal (e.g., sheet titanium) may be approximately 0.5 mm, although other thicknesses may also be suitable and used embodiments in accordance with the present invention.

In selected embodiments, an underside of a main body 18 may be concave. For example, a bottom surface of the skirting 23 of a main body 18 may define a concavity. This may enable an underside of a main body 18 to closely track, follow, or abut a corresponding end (e.g., a distal end) of a stump casting 12 when the main body 18 is applied thereto. That is, a distal end of a stump casting 12 may have a convex shape. Accordingly, a main body 18 with a concave shape may more closely match and/or follow the contour of a stump casting 12.

When a main body 18 with a concave underside is combined with pivoting flanges 20 that support bending 30, the end result may be a socket adaptor 14 that more easily and tightly conforms to the shape of a stump casting 12. This may enable a binding material 16 (e.g., a composite overwrap material) to more easily and completely engage the socket adaptor 12 and form a stump socket 10 that closely and/or tightly fits a stump casting 12 (and, as a result, the patient from whom the stump casting 12 was derived) without any gaps, voids, or pockets (e.g., air gaps between a stump casting 12 and the resulting laminated stump socket 10) that would weaken the end product 10. Accordingly, in use, a laminated stump socket 10 in accordance with the present invention may readily resolve all necessary or anticipated stresses without failure.

Referring to FIGS. 4-7, in selected embodiments, a main body 18 may be shaped to support various configurations of flanges 20. For example, as shown in the illustrated embodiments, a main body 18 may include seven pivot points 28 (e.g., bar 28, dowel 28, or the like) to which a flange 20 may be pivotably connected. In certain embodiments, a flange 20 may be connected to each such pivot point 28. Alternatively, flanges 20 may be connected only to selected pivot points 28.

In selected embodiments, four flanges 20 may be connected to a main body 18. For example, a first flange 20 may be connected to a first pivot point 28a, no flange 20 may connect to a second pivot point 28b, a second flange 20 may be connected to a third pivot point 28c, no flange 20 may connect to a fourth pivot point 28d, a third flange 20 may be connected to a fifth pivot point 28e, no flange 20 may connect to a sixth pivot point 28f, and a fourth flange 20 may be connected to a seventh pivot point 28g.

In other embodiments, three flanges 20 may be connected to a main body 18. For example, no flange 20 may connect to a first pivot point 28a, a first flange 20 may be connected to a second pivot point 28b, no flange 20 may connect to a third pivot point 28c, a second flange 20 may be connected to a fourth pivot point 28d, no flange 20 may connect to a fifth pivot point 28e, a third flange 20 may be connected to a sixth pivot point 28f, and no flange 20 may connect to a seventh pivot point 28g. Accordingly, a single main body 18 (i.e., various main bodies 18 of a single or shared design) may be used in four-flange embodiments, three-flange embodiments, or the like.

In selected embodiments, a prosthetist may select how many flanges 20 to connect to a main body 18 and which pivot points 28 are to receive one of those flanges 20. For example, a main body 18 may be supplied with a selected number of unattached flanges 20 (e.g., three to seven unattached flanges 20). Accordingly, a prosthetist may decide how many of the supplied flanges 20 are to be used. The prosthetist may also select which pivot points 28 are to receive a flange 20. A connection between a flange 20 (e.g., a proximal end of a flange 20) and a main body 18 may be such that the prosthetist may simply clip the flanges 20 to the pivot points 28 as desired. Accordingly, a socket adaptor 14 in accordance with the present invention may be configured on site in whatever manner is desired by a prosthetist (e.g., even a flange-free arrangement where only a main body 18 is incorporated into the stump socket 10).

In certain embodiments, various voids 31, indentations 31, windows 31, apertures 31, or the like may be formed in a main body 18, one or more flanges 20, or some combination thereof. For example, a plurality of apertures 31 may be distributed circumferentially around a main body 18 (e.g., within an outer skirting 23 of a main body 18). Certain such apertures 31a may provide locations for flanges 20 to engage a main body 18. For example, certain such apertures 31a may aid in creating, defining, or setting off one or pivot points 28. Other apertures 31b formed in a main body 18 may not correspond to any flanges 20 or engagements therewith. These other apertures 31b (as well as one or more apertures 31 in one or more flanges 20) may lighten a socket adaptor 14 (e.g., reduce an amount of metal contained in a socket adaptor 14) and/or provide locations that enable binding material 16 (e.g., a composite overwrap material) to more easily and completely engage, grip, or bond with a main body 18, flange 20, or the like.

Referring to FIG. 8-11, in selected embodiments, a loop 26, hook 26, or the like may be a monolithic extension of the rest of a flange 20. That is, a flange 20, including the loop 26, hook 26, or the like, may be formed (e.g., be cut and bent) from a single sheet of material. Alternatively, a flange 20 may comprise multiple components. For example, a flange 20 may include a main portion 32 and a loop or hook portion 26.

A hook portion 26 may be connected to a main portion 32 in any suitable manner. In certain embodiments, a loop or hook portion 26 may be welded to a main portion 32. In other embodiments, a loop or hook portion 26 may be connected to a main portion 32 via one or more rivets or other fasteners that extend through one or more apertures 34 that extend through the loop or hook portion 26 and the main portion 32.

Referring to FIGS. 18-25, in selected embodiments, one or more apertures 31 extending through the skirting 23 of a main body 18 may be circular in shape. For example, one or more apertures 31a that define or support pivot points 28 may be circular in shape. A circular shape may be formed quickly and easily using a drill bit in a machining process. Accordingly, apertures 31 that are circular in shape may enable a socket adaptor or one or more components 18, 20 thereof to be formed in a quicker or more cost effective manner.

Referring to FIGS. 26-30, in selected embodiments, a flange 20 may comprise a main portion 32 and a loop or hook portion 26 that are monolithically formed. For example, a main portion 32 and a loop or hook portion 26 may be monolithically formed of a single piece of sheet metal that is cut to shape and then bent at one end thereof to form a loop or hook portion 26.

Figure 31:
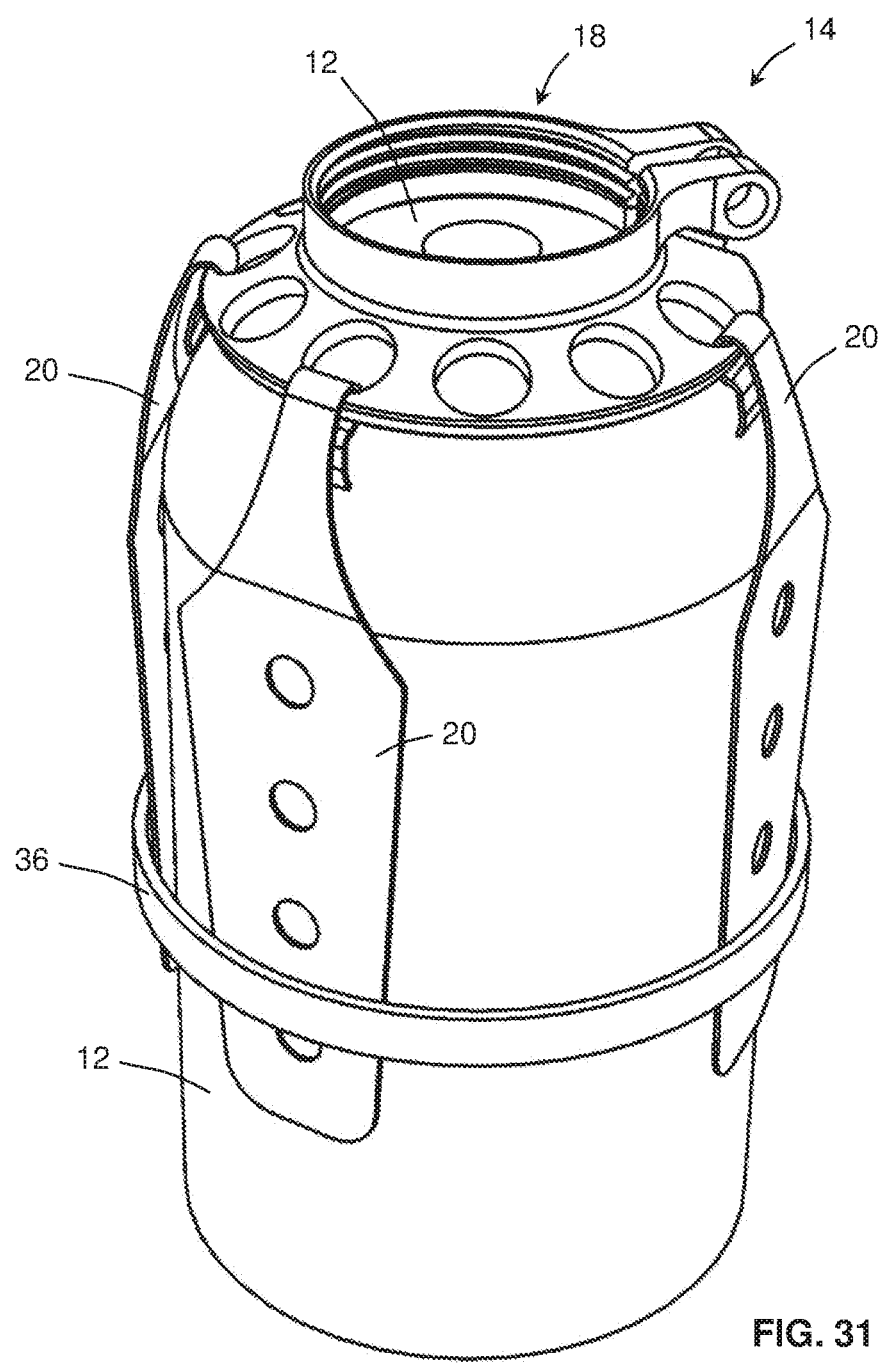
FIG. 31 is a perspective view a socket adaptor positioned on a stump casting in accordance with the present invention, wherein the socket adaptor comprises the main body of FIG. 18 and multiple instances of the flange of FIG. 26.

Referring to FIG. 31, in selected embodiments, pivoting of one or more flanges 20 with respect to a main body 18 may enable a socket adaptor 14 to conform closely to a stump casting without requiring much bending of the flanges 20. In certain embodiments, a socket adaptor 14 may be provided with a band 36 (e.g., an elastic band) that may be applied to hold one or more flanges 10 (e.g., a distal end or portion of one or more flanges 20) against a stump casting 12 while a prosthetist applies or begins applying a binding material 16. A band 36 may have sufficient strength and/or resilience to deflect the one or more flanges 20 and hold them against a stump casting 12. A band 36 may also hold the flanges 20 in positions where the various loops or hook portions 26 thereof are firmly engaging the main body 18 (i.e., where there is no unwanted slack between the flanges 20 and the main body 18).

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of forming a stump socket, the method comprising:
    obtaining a stump casting;
    obtaining a socket adaptor comprising
        a main body comprising a core and a skirting connected to the core, the core have a central aperture extending in an axial direction therethrough, the skirting extending away from the core and at least partially encircling the core, the skirting comprising a plurality of flange apertures extending therethrough, and
        one or more flanges, each of the one or more flanges comprising a proximal end and a distal end, wherein the proximal end pivotably connects to the main body and the distal end extends away from the main body, the proximal end pivotably connecting to the main body by extending through a corresponding flange aperture of the plurality of flange apertures to at least partially encircle an outer edge of the skirting;
    positioning the socket adaptor on a distal end of the stump casting, wherein the positioning comprises pivoting of the one or more flanges with respect to the main body to conform the socket adaptor to the stump casting;
    applying a binder material to encapsulate the socket adaptor and rigidly fix each of the one or more flanges with respect to the main body; and
    forming, by the binder material after the applying, a hardened outer shell of the stump socket.

2. The method of claim 1, wherein the positioning further comprises bending one or more of the one of more flanges to conform the socket adaptor to the stump casting.

3. The method of claim 1, wherein each flange aperture of the plurality of flange apertures extends in the axial direction through the skirting.

4. The method of claim 3, wherein a middle portion of each flange of the one or more flanges has a width that is greater than a diameter of every flange aperture of the plurality of flange apertures and the proximal end of each flange of the one or more flanges has a width that is less than the diameter of every flange aperture of the plurality of flange apertures.

5. The method of claim 4, wherein:
    the skirting forms a concavity; and
    the positioning comprises inserting the distal end of the stump casting into the concavity.

6. The method of claim 5, wherein the one or more flanges comprises three flanges substantially evenly distributed around the main body.

7. The method of claim 5, wherein the one or more flanges comprises four flanges substantially evenly distributed around the main body.

8. A method of forming a stump socket, the method comprising:
- obtaining a stump casting;
- obtaining a socket adaptor comprising
    - a main body having a core, a central aperture extending through the core in an axial direction, a skirting at least partial encircling the core, and a plurality of apertures extending through the skirting in the axial direction, and
    - one or more flanges, each of the one or more flanges comprising a proximal end and a distal end, wherein the distal end extends away from the main body and the proximal end extends through a different aperture of the plurality of apertures to at least partially encircle an outer edge of the skirting and thereby pivotably connect the each flange to the main body;
- positioning the socket adaptor on a distal end of the stump casting, wherein the positioning comprises pivoting of the one or more flanges with respect to the main body to conform the socket adaptor to the stump casting;
- applying a binder material to encapsulate the socket adaptor and rigidly fix each of the one or more flanges with respect to the main body; and
- forming, by the binder material after the applying, a hardened outer shell of the stump socket.

9. The method of claim 8, wherein the positioning further comprises bending one or more of the one of more flanges to conform the socket adaptor to the stump casting.

10. The method of claim 8, wherein:
- the skirting forms a concavity; and
- the positioning comprises inserting the distal end of the stump casting into the concavity.

11. The method of claim 8, wherein the one or more flanges comprises three flanges substantially evenly distributed around the main body.

12. The method of claim 8, wherein the one or more flanges comprises four flanges substantially evenly distributed around the main body.

13. The method of claim 8, wherein the obtaining the socket adaptor comprises:
- selecting how many flanges are to be included within the one or more flanges;
- selecting a location where each flange of the one or more flanges is to connect to the main body; and
- pivotably connecting each flange of the one or more flanges to the location selected therefore.

* * * * *